US006635704B2

(12) United States Patent
Engel et al.

(10) Patent No.: US 6,635,704 B2
(45) Date of Patent: *Oct. 21, 2003

(54) ORGANIC PARTICULATE-FILLED ADHESIVE

(75) Inventors: Michael R. Engel, Maplewood, MN (US); Chung I. Young, Roseville, MN (US); Michael Govek, Minneapolis, MN (US); Michael D. Delmore, Grant, MN (US); Michael R. Stumpf, St. Paul, MN (US); Chi-Ming Tseng, Woodbury, MN (US); Michael L. Ruegsegger, Mahtomedi, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/997,150

(22) Filed: Nov. 29, 2001

(65) Prior Publication Data

US 2002/0058754 A1 May 16, 2002

Related U.S. Application Data

(63) Continuation of application No. 09/504,683, filed on Feb. 16, 2000, which is a continuation-in-part of application No. 09/441,580, filed on Nov. 17, 1999, now abandoned.

(51) Int. Cl.⁷ .................................................. C08K 3/00
(52) U.S. Cl. ........................................ 524/503; 524/522
(58) Field of Search ................................. 524/503, 522

(56) References Cited

U.S. PATENT DOCUMENTS

| 3,441,430 A | 4/1969 | Peterson .................... 117/68.5 |
| 3,825,379 A | 7/1974 | Lohkamp et al. ............. 425/72 |
| 3,849,241 A | 11/1974 | Butin et al. ................. 161/169 |
| 3,865,770 A | 2/1975 | Blake ........................ 260/27 R |
| 4,295,809 A | 10/1981 | Mikami et al. ............... 425/72 |
| 4,375,718 A | 3/1983 | Wadsworth et al. .......... 29/592 |
| 4,413,080 A | 11/1983 | Blake ........................ 524/187 |
| 4,818,463 A | 4/1989 | Buehning ................... 264/40.1 |
| 4,986,743 A | 1/1991 | Buehning ....................... 425/7 |
| RE34,279 E | 6/1993 | Blake .......................... 524/145 |
| 5,270,111 A | 12/1993 | D'Haese et al. ............. 428/356 |
| 5,380,779 A | 1/1995 | D'Haese ..................... 524/272 |
| 5,512,277 A | 4/1996 | Uemura et al. ........... 424/78.03 |
| 5,512,612 A | 4/1996 | Brown et al. ................ 523/218 |
| 5,723,138 A | 3/1998 | Bae et al. .................... 424/401 |
| 5,935,596 A | 8/1999 | Crotty et al. ................ 424/448 |
| 5,939,093 A | 8/1999 | Park et al. ................... 424/443 |
| 5,952,420 A | 9/1999 | Senkus et al. ............... 524/548 |

FOREIGN PATENT DOCUMENTS

| EP | 0 692 240 | 1/1996 |
| EP | 0 947189 | 2/1998 |
| JP | 10-324613 | 12/1998 |
| WO | WO 96/38128 | 12/1996 |
| WO | WO 97/08260 | 3/1997 |
| WO | WO 97/32567 | 9/1997 |
| WO | WO 98/05283 | 2/1998 |
| WO | WO 98/06375 | 2/1998 |
| WO | WO 99/29795 | 6/1999 |

OTHER PUBLICATIONS

PCT International Search Report PCT/US00/29604 mailed Jun. 11, 2001.
Annex to Form PCT/ISA/206 Communication relating to the results of the partial International Search of PCT/US00/29604.

*Primary Examiner*—Edward J. Cain
(74) *Attorney, Agent, or Firm*—Scott R. Pribnow; Xen T. Florozak

(57) ABSTRACT

An organic particulate-filled adhesive is provided comprising ionomeric particulate dispersed in a polymer matrix containing water-soluble polymer or water-dispersible polymer. The adhesive preferably contains a plasticizer. If desired, in some formulations, the adhesive can contain additives, such as opacifying agents, skin cleansers, skin moisturizers, vitamins, and herbal extracts. The adhesive can have pressure sensitive adhesive properties, although such properties are not necessary. The adhesive can be formulated so as to be useful as a repulpable adhesive and as a cosmetic adhesive.

25 Claims, 1 Drawing Sheet

ORGANIC PARTICULATE-FILLED ADHESIVE

CROSS REFERENCE TO RELATED APPLICATION

This application is a continuation of U.S. Ser. No. 09/504,683, filing date Feb. 16, 2000 which is a continuation-in-part of U.S. Ser. No. 09/441,580, filed Nov. 17, 1999 abandoned.

TECHNICAL FIELD

This invention relates to organic particulate-filled adhesives containing ionomeric particulate and a polymer matrix. The ionomeric particulates are made from a suspension polymerization process. Depending on the particular ionomeric particulate composition and the particular polymer matrix, a wide variety of adhesives can be formulated. Particularly useful adhesives include repulpable adhesive and cosmetic adhesive.

BACKGROUND

Adhesives have been made using beads made from suspension polymerization. For example, U.S. Pat. No. 5,952,420 (Senkus et al.) discloses permeable, self-supporting shaped structures that can be used in applications such as filters, masks, or respirators. The structure comprises a mass of active particulate (e.g., sorbents such as activated carbon, silica gel, or alumina granules) bonded together with pressure sensitive adhesive polymer particulates (also referred to as "PSA suspension beads").

Adhesives have been formulated for application to skin for consumer cosmetic needs, such as skin cleansing or moisturizing. For example, U.S. Pat. No. 5,723,138 (Bae et al.) discloses a cosmetic composition having adhesive properties useful for alleviating wrinkles or furrows on skin. The composition is prepared by coating active ingredients comprising vitamin A, vitamin E, and aloe extract together with an adhesive on a non-toxic carrier.

U.S. Pat. No. 5,512,277 (Uemura et al.) discloses a keratotic plug remover composition and a method for removing keratotic plugs from the skin. Others skilled in the art have pursued different avenues to remove keratotic plugs, such as those disclosed in U.S. Pat. No. 5,939,093 (Park et al.). Other references that disclose keratotic plug removers include WO 98/06375, WO 98/05283, and WO 97/32567.

U.S. Pat. No. 5,935,596 (Crotty et al.) discloses a cosmetic product that delivers skin actives (such as vitamins, herbal extracts, alpha- and beta-hydroxycarboxylic acids, etc.) through adhesive strips. The strips can concurrently remove keratotic plugs from skin pores. The cosmetic product includes an adhesive polymer that may either be anionic, cationic, nonionic, amphoteric, zwitterionic, or mixtures thereof.

U.S. Pat. No. 5,512,612 (Brown et al.) discloses a pressure sensitive adhesive comprising a blend of (a) a polymeric, elastomeric, solvent insoluble but solvent dispersible microparticle component; and (b) a water-dispersible polymeric component. The adhesive is repulpable when tested according to TAPPI test UM-213.

While the foregoing adhesives may be useful for their intended applications, other adhesive compositions are sought.

SUMMARY

This invention provides novel organic particulate-filled adhesives. The adhesives can be formulated for various applications, such as for cosmetic applications and for repulpable adhesive applications. In brief summary, the organic particulate-filled adhesive comprises ionomeric particulates dispersed in a polymer matrix containing water-soluble polymer or water-dispersible polymer. The polymer matrix functions as a continuous phase binding the ionomeric particulates together. Additional components can be added to the adhesive including, but not limited to, plasticizers, opacifying agents, skin conditioning agents, and skin cleansing agents. In one embodiment of the invention, the adhesive contains at most about 40 parts by weight of a plasticizer commonly referred to as a "tackifier" (based on the polymer matrix weight), in which case the adhesive is particularly useful as a cosmetic adhesive. In another embodiment of the invention, the adhesive contains at least 40 parts by weight of a plasticizer (based on the polymer matrix weight that is a water-soluble polymer), in which case the adhesive is particularly useful as a repulpable adhesive.

In a cosmetic application, a user, i.e., a consumer, typically wets the skin where cleaning is desired and applies a cosmetic strip containing the inventive adhesive coated to a backing. Alternatively, the user wets the cosmetic strip with a small amount of water and applies the moistened strip to the skin. In a cosmetic strip application, it is the exposure of the organic particulate-filled adhesive to water that gives it pressure-sensitive adhesive properties. After a duration of time, which can range from about 1 to 20 minutes, the user pulls the strip away from the skin thereby removing unwanted matter such as comedomes, unwanted hair follicles, dirt, oil, dead skin, and debris. In a repulpable adhesive application, the inventive adhesive preferably does not interfere with the paper manufacturing process. Also, the adhesive components are preferably dispersed in the paper to minimize defects.

BRIEF DESCRIPTION OF THE DRAWINGS

The invention is further explained with reference to the drawings, wherein.

Figure 1:
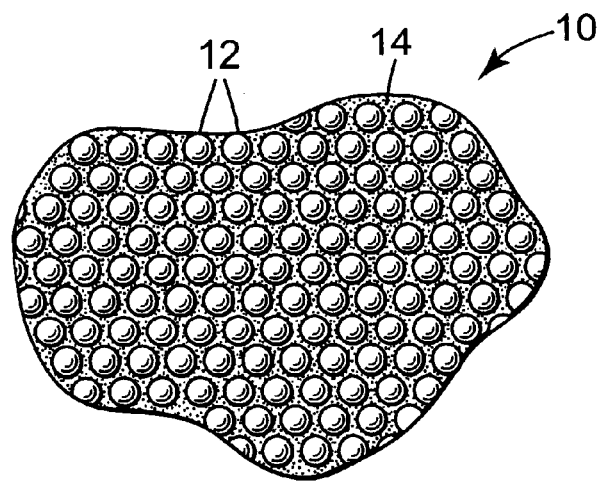
FIG. 1 is an illustrative, greatly enlarged, schematic, planar view of a representative portion of the inventive organic particulate-filled adhesive 10 containing ionomeric particulates 12 dispersed in a polymer matrix 14.
Figure 2:
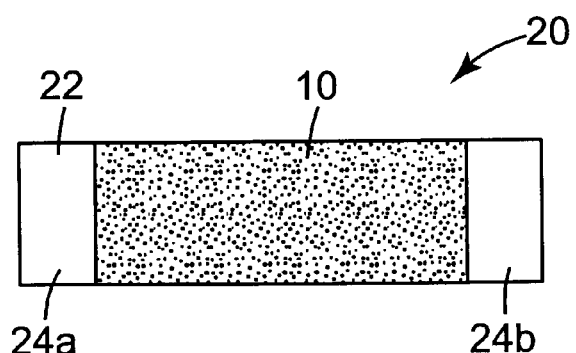
FIG. 2 is a schematic of one embodiment of the invention, a cosmetic strip 20 containing the organic particulate-filled adhesive 10 applied to a flexible backing 22, and containing tabs 24a and 24b for convenient removal of from the skin, the tabs containing little to no adhesive thereon.

These figures are idealized, are not to scale, and intended to be merely illustrative and non-limiting.

Definitions

As used herein,

"Cosmetic adhesive" means generally one that is capable of being applied to mammalian skin (in particular, human skin) for the main purpose of removing undesirable materials, e.g., comedomes, unwanted hair follicles, dirt, debris (such as dead skin), and oil.

"Ionomeric particulate" means a polymer particle (typically in spherical form), having an oleophilic rich core and a surface that is rich in inorganic salt groups (such as zinc salt) attached to a polymer chain.

"Monomer surfactant" acts as a surfactant in that it aids in the initial formation of the polymer bead during suspension polymerization but it is believed that at least a portion of the surfactant polymerizes and becomes a part of the ionomeric particulate. Also, at least a portion of the surfactant polymerizes in the water phase.

Unless otherwise specified, "parts by weight" denotes the amount of the particular component as a percentage of all the components in the final adhesive composition.

"Repulpable adhesive" means generally one that is used in manufacture of paper. Preferably, the adhesive does not interfere with the manufacturing process or with the paper produced from the process. Preferably, the components of the repulpable adhesive (1) are not incorporated into the paper or (2) are sufficiently dispersed in the paper such that any defects that may be attributed to the adhesive are below the limits of visual detection. Illustrative repulpability test methods include TAPPI test UM-213, and the Japanese Repulpablilty Test, as described in the Test Method Section below.

"Water-dispersible polymer" refers to a polymer that when exposed to water creates a two-phase system, where one phase contains finely divided polymer particles distributed throughout the second phase, which is water. The particles form the disperse phase.

"Water-soluble polymer" refers to macromolecules exhibiting solubility in aqueous solutions. Preferably, the water-soluble polymer is nearly completely soluble in the aqueous solution.

"Solubility" means generally the ability of one substance (the water-soluble polymer) to blend uniformly with another substance (the water).

DETAILED DESCRIPTION OF THE INVENTION

The inventive adhesive contains two main components: (1) an ionomeric particulate composition dispersed in (2) a polymer matrix, which can be water-soluble polymers or water-dispersible polymers. Plasticizers are preferably added to the adhesive. Additives can be incorporated in the adhesive include opacifying agents, skin cleansing agents, and moisturizing agents. The components and the additives are discussed in detail below.

The inventive organic particulate-filled adhesive preferably contains at most 50 parts, more preferably, about 5 to 40 parts by weight of a polymer matrix. The polymer matrix contains water-soluble polymers or water-dispersible polymers. The polymer matrix acts as the continuous phase to bind the ionomeric particulates together. Ionomeric particulates are added to modify the polymer matrix because the latter can often lack desirable properties, such as flexibility, elasticity, adhesion, cohesive strength, toughness, and, in certain applications, skin cleaning efficacy.

Useful water-soluble polymers include, but are not limited to, polyacrylic acid, salts of polyacrylic acid, polymethacrylic acid, salts of polymethacrylic acid, sulfonated polyester, polysodium styrene sulfonate, polyethylene oxide, polyvinyl pyrrolidone, gamma radiation modified polyvinyl pyrrolidone, polyvinyl alcohol, and tertiary amine containing polymers, such as polydimethylamino methacrylate. Another class of useful water-soluble polymer includes those containing carboxylic acid or anhydride containing copolymers. Commercially available ones include Gantrez® series (e.g., Gantrez® S-97, Gantrez® AN-139, Gantrez® ES-225, and Gantrez® ED-425) from International Specialties Products, Wayne, N.J., which are believed to be copolymers of methyl vinyl ether and maleic anhydride. Yet another useful water-soluble polymer includes polysodium 2-acrylamido-2-methylpropane sulfonate (poly-AMPS™). Combinations of the various listed water-soluble polymers can be used.

A particularly useful water-soluble polymer is polyacrylic acid (PAA). Useful molecular weight for the PAA and blends of PAA fall in the range of about 20,000 to 750,000. For cosmetic application, the PAA molecular weight is preferably about 100,000 to 500,000. For repulpable adhesive application, the PAA or blends of PAA preferably have a molecular weight of about 200,000 to 500,000.

Useful water-dispersible polymers include water-dispersible adhesives, such as those disclosed in U.S. Pat. Nos. 5,380,779 (D'Haese); 5,270,111 (D'Haese et al.); 4,413,080 (Blake); 3,865,770 (Blake); and RE 34,279 (Blake). When using water-dispersible adhesives as the continuous phase, plasticizers may not be needed.

The inventive organic particulate-filled adhesive preferably contains at least 50 parts, more preferably about 60 to 95 parts by weight of the ionomeric particulates. Ionomeric particulate compositions and method of making the same can be found in Assignee's copending U.S. applications Ser. No. 09/441,556 and Ser. No. 09/441,578, which are hereby incorporated by reference, both applications filed on Nov. 17, 1999.

In brief summary, the method of making an ionomeric particulate of the invention comprises or consists essentially of (a) forming an aqueous phase comprising an acid monomer, a metal oxide, and at least a first and a second surfactant, the first being a monomer surfactant; (b) forming an oil phase comprising at least one vinyl monomer; and (c) suspension polymerizing the oil phase. Bulk polymerization can be carried out in suspended droplets. Typically, it is desirable to keep the droplets from coalescing as they proceed from a liquid to a solid state. Optional components such as polyacrylamide can be added to the aqueous phase to help control the particulates' size. Also, an initiator is added to the oil phase to start the polymerization. Each of these components is discussed in detail below.

The vinyl monomers is preferably present in an amount of at least 80 parts, more preferably about 85 to 95 parts, based on 100 parts total monomer content. Vinyl monomers can be straight chain, branched, or cyclic. One class of vinyl monomers useful in the present invention include monofunctional unsaturated acrylate ester monomers, of which a preferred class includes acrylic acid ester of non-tertiary alcohol having 1 to 14 carbon atoms. Included within the preferred class of acrylate monomers are, e.g., isooctyl acrylate (IOA), isononyl acrylate, 2-ethylhexyl acrylate, decyl acrylate, dodecyl acrylate, n-butyl acrylate, hexyl acrylate, hydroxyethyl acrylate (HEA), hydroxyethyl methacrylate (HEMA), and combinations thereof. Other preferred vinyl monomers include vinyl acetate, styrene, octylacrylamide, and N-vinyl lactams such as N-vinyl pyrrolidone and N-vinyl caprolactam. These latter vinyl monomers can be used in combination with the above described acrylate monomers.

The initiator is preferably present in an amount of about 0.05 to 1 part based on 100 parts total monomer weight. Useful initiators for polymerizing the vinyl monomers include those suitable for free-radical polymerization of the vinyl monomers. The initiators are preferably oil-soluble and have low solubility in water. Illustrative examples of useful initiators include organic peroxides such as benzoyl peroxide, lauryl peroxide, and various thermal initiators such as 2,2'-azobisisobutyronitrile. A preferred thermal initiator is 2,2'-azobis(2-methylbutyronitrile), commercially available from E. I. Du Pont de Nemours and Co., Wilmington, Del., under the trade name VAZO™ 67.

The acid monomer is present in an amount up to about 20 parts based on the total monomer content. Acid monomers useful in for this invention preferably contain a carboxylic acid group. Acid monomers useful for the practice of this invention include acrylic acid, methacrylic acid, itaconic acid, maleic acid, fumaric acid, and citraconic acid. Preferred acid monomers include acrylic acid and methacrylic acid.

At most, the metal oxide is present in an amount necessary to fully neutralize the acid functionality of the acid monomer. For example, in one inventive composition, the metal oxide is zinc oxide and the acid monomer is methacrylic acid. To have a "fully neutralize" particulate requires up to one (1) mole of zinc oxide per two (2) moles of methacrylic acid.

A fully neutralized ionomeric particulate can be used to tailor the interaction between the particulates and the polymer matrix. Also, in some applications, a fully neutralized ionomeric particulate is used as a component in an organic particulate-filled adhesive that desirably has little to no interaction with the substrate to which the adhesive is applied. This situation is particularly important if the substrate may contain acid sensitive groups on its surface. If, on the other hand, the organic particulate-filled adhesive contains ionomeric particulate that has acid functional groups, there may be some interaction between the adhesive and the substrate containing acid sensitive groups. This interaction could result in leaving residual adhesive on the substrate, an undesirable result when clean removal of the adhesive is a desired feature.

In some applications, the ionomeric particulate can have acid functionality, which arises when the acid monomer is not fully neutralized. Thus, the metal oxide can be used to tailor the functionality of the ionomeric particulate. One skilled in the art should take care in selecting a suitable polymer matrix when making the organic particulate-filled adhesive given the different functionality of the ionomeric particulate. In other words, a polymer matrix suitable for fully neutralized ionomeric particulates may not be suitable for ionomeric particulate containing acid functional groups.

Although zinc oxide (ZnO) is preferred, other useful metal oxides include calcium oxide (CaO) and magnesium oxide (MgO). It is believed that the metal oxides react with the acid monomer to form metal ionic salts of acid monomer.

Surfactants are preferably present in an amount of about 3 to 10 parts based on the total monomer content. There are at least two types of surfactants that are useful in this invention. The first type can be referred to as a monomeric surfactant. The second type can be referred to as conventional surfactants, which include those selected from the group consisting of non-ionic surfactant, anionic surfactant, and mixtures thereof.

Examples of the monomer surfactant include sodium styrene sulfonate. Monomer surfactants not only function like conventional surfactants in suspension polymerization by aiding in the formation of suspension beads and minimizing coalescence of the beads, but it is believed that at least a portion of the surfactant can polymerize and become a part of the ionomeric particulate. Because monomer a surfactants can be polymerized, there may be little residue of these surfactants in the aqueous phase. In this respect, monomer surfactants differ from conventional surfactants.

Useful conventional surfactants that are non-ionic have a HLB (Hydrophilic-Lipophilic Balance) from about 1 to 15. The HLB number describes the balance of the size and strength of the hydrophilic (water-loving or polar) groups and lipophilic (oil-loving or non-polar) groups of the surfactant. Illustrative useful non-ionic surfactants include (1) polyethers, e.g., ethylene oxide and propylene oxide condensates, which include straight and branched $C_2$ to $C_{18}$ alkyl, alkylaryl, and alkenyl alcohol based copolymers of ethylene oxide and propylene oxide, such as those from Union Carbide Co., Danbury, Conn., under the trademarked TERGITOL series, (2) block copolymers of ethylene oxide and propylene oxide, such as those available from BASF Co., Mt. Olive, N.J., under the trademarked PLURONIC and TETRONIC series. Other suitable non-ionic surfactants are the TWEEN and SPANS, trademarked compositions from ICI Surfactants, Brantford, Ohio, which are believed to be polyoxyalkylene derivatives of sorbitan and fatty acid esters.

Useful conventional surfactants that are anionic include sulfates or sulfonates, such as sodium alkylaryl sulfonates and poly(alkyleneoxy) sulfates or sulfonates. A preferred sodium alkylaryl sulfonate is sodium dodecylbenzene sulfonate, which is commercially available from Rhone-Poulenc as Rodacal™ DS-10. The poly(alkyleneoxy) compounds are ethylene oxide and propylene oxide or ethylene oxide and butylene oxide condensates, which include straight and branched $C_2$ to $C_{18}$ alkyl, alkylaryl, and alkenyl alcohol based copolymers of ethylene oxide and propylene oxide or ethylene oxide and butylene oxide. This anionic surfactant is available from BASF Co. under the tradename MAZON SAM™ 211, which is an alkylene polyalkoxy sulfate.

Polyacrylamide is preferably present in an amount of about 0.01 to 2 parts based on the total monomer content and forms part of the water phase. In general, the polyacrylamide functions as a stabilizer to produce ionomeric particulate of smaller size. It has been discovered that use of the polyacrylamide in combination with the anionic surfactants above can produce ionomeric particulate with less than about 10 micrometers in size. Thus it is not necessary to rely on the conventional homogenization process to make ionomeric particulate with less than 10 micrometer in volume average diameter. Depending on the type of polyacrylamide used, however, larger particle size (on the order of (10 to 100 micron) can be produced. Preferred polyacrylamides are available from Cytec Industries, Inc., West Paterson, N.J. under the trademarks CYANAMER N-300 and CYANAMER P-35. It is surprising that such a small amount of polyacrylamide can help to control the particulates' size.

Suspending agents are preferably present in an amount of about 0.005 to 5 parts based on the total monomer content. In general, these agents are used in suspension polymerization to minimize coalescence of the particles. They can be minimally water-soluble inorganic suspending agents, such as tribasic calcium phosphate, calcium carbonate, calcium sulfate, barium sulfate, barium phosphate, hydrophilic silicas, and magnesium carbonate. A preferred inorganic suspending agent is colloidal silica, such as Nalco™ 1042, available from Nalco Chemical Company.

Plasticizers can be used to impart properties such as softness, pliability, and tackiness to the organic particulate-filled adhesive. Useful plasticizers include polyethylene glycol, glycerin, polypropylene glycol, polypropylene glycol-polyethylene oxide copolymer, block copolymers of ethylene oxide and propylene oxide (such as those sold under the trademarked PLURONIC and TETRONIC series from BASF Co.), polyethylene oxide alkylphenyl ethers (such as those sold under the trademarked IGEPAL series from Rhone-Poulenc, Inc.), and water. The amount of plasticizer used in the adhesive depends on its intended application, the type of polymer matrix, and the type of plasticizer chosen.

For example, in a useful cosmetic strip, the organic particulate-filled adhesive preferably contains less than about 40 parts of the plasticizer, based on the weight of the polymer matrix, which is preferably a water-soluble polymer. The ratio of the amount of plasticizer to the amount of water-soluble polymer can be an important parameter to control in making a cosmetic adhesive. At a plasticizer level of less than about 40 parts, the cosmetic adhesive typically does not possess pressure sensitive adhesive properties.

It is within the practice of the present invention, however, to formulate a cosmetic strip containing organic particulate filled adhesive that has pressure sensitive adhesive properties by choosing the appropriate ionomeric particulate, the appropriate polymer matrix, and the appropriate amount of plasticizer, among other components.

In a useful repulpable adhesive application, the organic particulate-filled adhesive preferably contains more than about 40 parts by weight of the plasticizer, based on the weight of the polymer matrix, which is preferably a water-soluble polymer. At such a level of plasticizer, the repulpable adhesive is normally a pressure sensitive adhesive. If the polymer matrix is water-dispersible, then a plasticizer may not be needed.

In addition to the ionomeric particulate, additives can be used to further modify the polymer matrix and impart to the inventive adhesive some desired property. These additives can be used in the cosmetic adhesives. Examples of useful additives include opacifying agents, skin cleansers, skin moisturizers. Other useful additives includes vitamins (such as Vitamin A, Vitamin B, Vitamin C, Vitamin E, and combinations thereof), herbal extracts (including antioxidants and free-radical inhibitors); alpha- and beta-hydroxoycarboxylic acids, and anti-inflamatories, all of which are described in U.S. Pat. No. 5,935,596 (Crotty et al.). If used, these agents can be present in an amount of about 0.001 to 10 parts by weight.

Opacifying agents can be used in the organic particulate-filled adhesive to impart color, if desired. For example, in a cosmetic application, it may be desirable to have a nearly white colored adhesive to provide color contrast between the adhesive and the undesirable materials. Those skilled in the art have used inorganic fillers, such as titanium dioxide, calcium carbonate, and the like to color their adhesives. These inorganic fillers, however, tend to be basic, and it has been found that they can affect the rheology of the inventive adhesive negatively, e.g., by changing the viscosity of the adhesive.

It has been discovered that the use of styrene-acrylic copolymer hollow particles is especially useful in formulating cosmetic adhesives. This advantage occurs because the copoloymer particles do not have a negative effect on the rheology of the adhesive. If used, the opacifying agent is preferably present in an amount of about 0.05 to 10.0 parts by weight. A preferred styrene-acrylic copolymer hollow particle is commercially available as ROPAQUE® OP-96 from Rohm and Haas Co. Although ROPAQUE® OP-96 has been used to formulate paints, it is believed that this is the first time it has been used in a cosmetic application.

It has been found that the use of metal salts, such as metal citrates, metal lactates, and metal chlorides, have been helpful in further toughening the polymer matrix, in addition to the ionomeric particulates. The metal salts are especially useful in cosmetic adhesives. It is believed that a cosmetic adhesive containing metal salts further minimizes any residue that may be left on a user's skin when the user removes the cosmetic strip. Suitable metal cations include magnesium, which is preferred, zinc and calcium. Preferred are the metal salts of citric acid. Metal salts of carboxylic acids can be used and a useful list is described in U.S. Pat. No. 5,935,596 (Crotty e al.) in column 4, lines 28 to 60. Any anionic counterion to the metal cations of the metal salts can be used as a toughening agent, so long as the compositions of the counterions are not toxic to the skin. If used, the cosmetic adhesive contains about 0.01 to 5 parts by weight of the metal salts.

Figure 3:
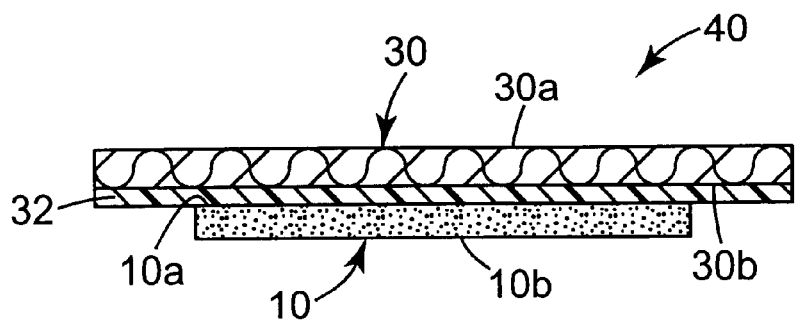
FIG. 3 is a cross-sectional view of another embodiment of the invention, a cosmetic strip 40.

FIG. 3 shows another illustrative embodiment of a cosmetic strip 40 comprising a hydrophobic coating 32 lying between a backing 30 and an organic particulate filled adhesive 10. As shown, the backing has first and second surfaces 30a and 30b respectively and the organic particulate filled adhesive has first and second surfaces 10a and 10b respectively. The hydrophobic coating 32 can be applied to at least one of the surfaces 30a, 30b, and 10a or a combination of these surfaces. In one preferred method, the hydrophobic coating is in solution form and can be applied to such surfaces through conventional coating methods, such as spray-coating, bar coating, and hand-coating.

As stated, in use, a consumer typically moistens his or her skin with a small amount of water prior to applying the cosmetic strip 40. This action causes surface 10b to become wet and the adhesive 10 becomes slightly solvated. In less than about 10 minutes, more likely in about 4 to 5 minutes, a portion to nearly all of the water has been absorbed and/or diffused through the cosmetic strip. The cosmetic strip appears and feels sufficiently dry to the consumer so as to be removed from the skin. Thereafter, the consumer removes the strip from his skin thereby removing unwanted materials.

Water that inadvertently gets on the backing 30 (e.g., from wet hands) may migrate toward the backing/adhesive interface and cause interlayer delamination between the backing 10 and the adhesive 30. It has been discovered use of a hydrophobic coating can provide some amount of water repellant properties so as to minimize interlayer delamination. The hydrophobic coating, however, does not need to provide complete water repellant properties, but only that amount necessary so as to minimize interlayer delamination to minimize the amount of adhesive residue left on the consumer's skin. In a preferred embodiment, enough hydrophobic material is used so as to leave little or no adhesive residue on the consumer's skin.

Suitable materials for use as the hydrophobic coating include any material exhibiting hydrophobicity such that when used on a particular backing, will modify the surface tension of the backing to keep the water from migrating or soaking into the backing. Illustrative hydrophobic coatings include fluoropolymers, fluorosilicones, and silicones. Other useful coatings include hydrocarbon waxes such as paraffin, polyethylene, polypropylene, polyethylene-acrylic acid copolymers, and montan ester-based emulsions. Yet other useful hydrophobic materials contain long chain alkyl pendant groups (e.g., $C_{18}$ alkyl groups) such as polyurethanes, urethane-acrylate copolymers, acrylate copolymers, and methacrylate copolymers. Commercially available material include Scotchguard™ product number 3572ES (from Minnesota Mining and Manufacturing, St. Paul, Minn.) and GE silicone water-based emulsions SM-2138 and SM 2059 (from General Electric, Waterford, N.Y.). Another useful material is disclosed in U.S. Pat. No. 2,532,011 (Dahlquist et al.).

Preferably, the hydrophobic coating provides the necessary water repellant properties but does not affect adversely the adhesion between the backing and the organic particulate filled adhesive. By not "affecting adversely," it is meant that the hydrophobic coating (1) does not decrease the interlayer adhesion between the backing and the organic particulate filled adhesive to such an extent that causes delamination of the adhesive off the backing, and yet (2) allows the water used to moisten the skin to be absorbed in or to migrate through the cosmetic strip in a sufficient amount of time, such as less than 20 minutes, preferably less than about 10 minutes, more preferably less than 5 minutes. Preferably, the hydrophobic coating is non-toxic to the user's skin.

Typically, the organic particulate-filled adhesive is disposed on a backing to yield a tape. The application of the adhesive determines the type of backing used. In most applications, the backing is preferably flexible. Suitable materials for use as backing materials include papers, treated papers, polymers, woven fibers, such as fabrics, or non-woven materials.

In a cosmetic application, the backings are typically woven fabrics and non-woven materials. Preferably, the flexible backing is non-occlusive and has sufficient strength to be removed from skin. The backing has a basis weight preferably in the range of about 5 to 80 grams/m$^2$, more preferably about 20 to 30 grams/m$^2$. Illustrative useful flexible backings include spunlaced non-woven, spun-bonded non-woven, polyurethane open-celled foams, carded web non-woven, blown microfiber non-woven, woven fabrics selected from the group consisting of cotton, acetate, polyester, rayon, and blends thereof. Useful commercially available flexible backings include the following: (1) spunlaced non-woven under the SONTARA® series from the Du Pont Company, Wilmington, Del., such as those under product number 8000 and 8017 (polyesters), 8423 (rayon/polyester blend), and 8841 (wood-pulp/polyester blend); (2) spunlaced non-woven rayon/polyester under VERATEC 140-093, from Veratec, Walpole, Mass.; (3) polyurethane open-cell foam under the trademark POLYCRIL® 200, 300, and 400 from Fulflex, Middletown, R.I.; (4) carded web non-woven, such as a 50/50 weight ratio blend of rayon fiber and acrylic binder or a 30/50/20 weight ratio blend of LENZING® rayon/Rohm and Haas ACRYLOID® B-15H/KOSA® HCT-254 polyester fiber (at 15% point bonding); (5) blown non-woven microfiber, such as 95/5 weight ratio blend of Morton polyurethane resin MORTHANE® PURPS440-200/Reed Spectrum titanium oxide concentrate (at 50% by weight TiO$_2$), blown non-woven polypropylene, and blown non-woven polyethylene; and (6) woven fibers, such as woven cotton from Conco Medical, Rocky Hill, S.C. and woven acetate from Milliken Company, Spartanburg, S.C.

In the repulpable adhesive application, the backing should also be repulpable, such as, e.g., paper backings.

The organic particulate-filled adhesive can be made by combining the polymer matrix with the ionomeric particulates, preferably adding the plasticizer, and any additives as desired. The method of making a repulpable adhesive and the method of making a cosmetic adhesive are discussed below.

In a method of making a repulpable adhesive, after the ionomeric particulate has been charged to a reactor and stirring has begun, the polymer matrix, which can be a water-soluble polymer or a water-dispersible polymer, is added. The polymer matrix may be a single component or blend of several polymers. The plasticizer, preferably polyethylene glycol, is added. The resulting dispersion can be coated onto, preferably, a paper backing using conventional coating methods, e.g., notch bar coating and gravure coating. The coated dispersion is dried to produce repulpable tape.

In a method of making a cosmetic adhesive, after the ionomeric particulate has been charged to a reactor and stirring at low speed has begun, the opacifying agent additive is added. A plasticizer is added. The polymer matrix, water-soluble polymer, is added to the mixture while stirring continues. The water-soluble polymer can be a single component or blend of several polymers. Optionally, a co-solvent is added to the dispersion.

Co-solvents function mainly to aid in the coating of the dispersion. Co-solvents do not generally become a constituent in the final cosmetic adhesive. Illustrative useful co-solvents include isopropanol, 1-propanol, ethanol, and combinations thereof. When used, the co-solvent is preferably present in an amount of about 1 to 20 parts, based on the total adhesive dispersion weight.

The dispersion can be coated on to a release liner (using conventional coating techniques, e.g., notch bar coating and gravure coating), and dried to form the cosmetic adhesive. The dispersion can be dried completely, nearly completely, or partially dried. The adhesive typically does not possess PSA properties, although in some formulations, it may have PSA properties. The adhesive is laminated to a flexible backing using conventional lamination techniques. If the adhesive was dried completely or nearly completely, it is preferable to moisten it slightly with deionized water. The moistened adhesive surface is then laminated to a desired flexible backing and this entire assembly is dried. In an alternate method of making a cosmetic adhesive, the dispersion is coated directly on to the desired flexible backing and dried.

In the methods described above, drying can be done by, e.g., forced air drying using ovens. Other drying methods can be used, depending on the adhesive dispersion formulation.

EXAMPLES

Examples 1a to 1d

Examples 1a to 1d showed the ionomeric particulates at various ZnO levels. The ionomeric particulates were made by a suspension polymerization reaction. The reaction was carried out in a 2-liter split-flask equipped with a condenser, thermometer, nitrogen inlet, motor-driven agitator, and a heating mantle with temperature control. The reaction flask was first charged with the ingredients of the aqueous phase, as shown in Table 1, and heated to 58° C. The batch of aqueous phase was maintained at this temperature with agitation and nitrogen-purging for about 1 hour to remove oxygen from the flask. Afterwards, a premixed charge of the oil phase, as shown in Table 1, was added to the flask while vigorous agitation (700 rpm) was maintained to obtain a good suspension. The ensuing suspension polymerization reaction was continued with nitrogen purging. After exotherm, the reaction was continued at 75° C. for about another 2 hours, and then the reaction mixture was cooled to room temperature. The ionomeric particulate composition was stored in aqueous form. The ionomeric particulates had a particle size of about 5 to 10 micrometers mean volume diameter. The suspension polymerization produced an aqueous suspension of ionomeric particulate having about 40% to 45% solids by weight.

TABLE 1

| Ionomeric Particulates | EXAMPLES | | | |
|---|---|---|---|---|
| Ingredients, grams: | 1a | 1b | 1c | 1d |
| Water phase: | | | | |
| Water (deionized) | 600 | 610 | 610 | 610 |
| Methacrylic acid | 20 | 25 | 25 | 25 |
| Zinc oxide | 2 | 5 | 7.5 | 10 |
| Colloidal silica[a] | 2 | 0 | 0 | 0 |
| Sodium styrene sulfonate | 20 | 25 | 25 | 25 |
| Sodium dodecylbenzene sulfonate[b] | 4.3 | 3.23 | 3.23 | 3.23 |
| Oil Phase: | | | | |
| 2-Ethyl hexyl acrylate | 380 | 475 | 475 | 475 |
| 2,2'-Azobis(methyl-butyronitrile)[d] | 1.6 | 2.0 | 2.0 | 2. |
| Volume average particle size, μm | 6.0 | 5.0 | 6.7 | 9.5 |

[a]Nalco ™ 1042 colloidal silica, from Nalco Chemical Company, Naperville, IL
[b]Rodacal DS-10 from Rhone-Poulenc, Cranbury, NJ
[c]Mazon SAM ™ 211, from BASF Co., Mt. Olive, NJ
[d]Vazo ™ 67 initiator, from du Pont de Nemours and Company, Wilmington, DE As used in all the examples herein, a "solids weight ratio" means the ratio of the components in the final adhesive that has been coated and dried.

Example 2

A 15% solids by weight solution of polyacrylic acid (PAA) having a molecular weight of about 450,000 (Carbopol® 907, from B. F. Goodrich, Cleveland, Ohio) was prepared by mixing the PAA with deionized water. To a vessel equipped with a mixing device, about 50 grams of the ionomeric particulate made according to Example 1c above was charged. About 64.3 grams of polyacrylic acid solution was added to the vessel. About 17.1 grams of isopropanol was added as a co-solvent. The resulting dispersion was allowed to rest at room temperature for at least several hours to remove the air bubbles, if any were present.

The dispersion made above was notch bar coated at a bar gap setting of about 0.84 mm onto a 0.051 mm thick (0.002 inch) release liner, which was a silicone coated polyester liner (product number E-936 liner from Akrosil Industrial Papers, Menasha, Wis.). The coating dried in an oven with at temperature setting of about 66° C. (150° F.) for about 15 minutes to yield a cosmetic adhesive having an exposed first surface and a second surface disposed on the liner. The adhesive coating weight was about 140 grams/m². The resulting cosmetic adhesive had a 30:70 solids weight ratio of PAA to ionomeric particulate.

The exposed surface of the cosmetic adhesive was moistened with a towel dampened with water. The moistened surface was immediately laminated at room temperature to a spunlaced non-woven polyester backing (SONTARA® 8017 from E. I. du Pont de Nemours and Company, Wilmington, Del.) so that the adhesive was sandwiched between the liner and the backing. Lamination was done by sending the sandwich through a nip created by a pair of rollers. The adhesive was embedded into the SONTARA® backing. The laminated adhesive was further dried in an oven with a temperature setting of about 66° C. for at most 10 minutes.

The cosmetic adhesive with its backing was die cut to yield a plurality of cosmetic strips. Several users wet the skin of their noses with water and applied the die cut strips. Each user waited about 4 minutes and then removed the strip from the skin. The cosmetic strips were efficacious in removing comedomes from the pores of the users' skin.

Example 3

To a vessel equipped with a mixing device, about 50 grams of ionomeric particulate made according to Example 1b was charged. About 38.6 grams of polyacrylic acid-sodium polyacrylate blend having a molecular weight of about 240,000 (Good-Rite® K-702, from B. F. Goodrich, Cleveland, Ohio, the blend being supplied at 25% solids by weight) was added into the vessel. About 8.9 grams of isopropanol was added as a co-solvent. The cosmetic adhesive composition contained about 27:73 solids weight ratio of PAA to ionomeric particulate. The dispersion and the cosmetic strips were made according to the methods described in Example 2 except that the backing material was a polyurethane resin blown microfiber non-woven. The backing was prepared by using a 95:5 solids weight ratio blend of polyurethane resin (Morthane® PS 440-200 from Morton International, a division of Rohm and Haas Co., Philadelphia, Pa.) and a pigment concentrate (about a 50:50 weight ratio blend of polyurethane resin and titanium dioxide from Clariant, Minneapolis, Minn.). The microfibers were prepared, in part, using the apparatus discussed in, e.g., Wente, Van A. "Superfine Thermoplastic Fibers," Industrial Engineering Chemistry, Vol. 48, pages 1342 to 1346 and in Wente, Van A. et al., "Manufacture of Superfine Organic Fibers," Report No. 4364 of the Naval Research Laboratories, published May 25, 1954, and the following U.S. Pat. Nos.: 3,849,241 (Butin et al.); 3,825,379 (Lohkamp et al.); 4,818,463 (Buehning); 4,986,743 (Buehing); 4,295,809 (Mikami et al.); or 4,375,718 (Wadsworth et al.).

The resulting backing had about 100 grams/meter² basis weight and about 23 micrometer fiber diameter. The adhesive coating weight was about 88 grams/m². All the cosmetic strips were efficacious in removing comedomes from the pores of the users' skin.

Example 4

To a vessel equipped with a mixing device, about 50 grams of ionomeric particulate made according to Example 1c was charged. About 61.7 grams of polyacrylic acid having a molecular weight of about 450,000 (Carbopol® 907 from B. F. Goodrich, Cleveland, Ohio, at about 15% solids by weight as prepared according to Example 2) was added while stirring was continued. About 0.39 grams of polyethylene glycol (PEG) plasticizer (Carbowax 600, from Union Carbide Co., Danbury, Conn.) was added to the vessel. About 16.8 grams of isopropanol was added as a co-solvent. The resulting dispersion and the cosmetic strips were made according to the method described in Example 2. The resulting cosmetic adhesive had about a 96:4 solids weight ratio of PAA to plasticizer and about a 30:70 solids weight ratio of PAA and PEG to ionomeric particulates. The adhesive coating weight was about 155 grams/m². The cosmetic strips were efficacious in removing comedomes from the pores of the users' skin.

Example 5

To a vessel equipped with a mixing device, about 50 grams of ionomeric particulate made according to Example 1a was charged. About 33.8 grams of polyacrylic acid having a molecular weight of about 450,000 (Carbopol® 907 containing about 15% solids by weight, from B. F. Goodrich, Cleveland, Ohio) was added while stirring was continued. About 0.56 grams of a glycerin plasticizer was added to the vessel. About 12.7 grams of isopropanol was added as a co-solvent. The resulting dispersion and the cosmetic strips were made according to the method described in Example 2 except that the backing used was that of Example 3. The resulting cosmetic adhesive had about a 90:10 solids weight ratio of PAA to plasticizer and about a 20:80 solids weight ratio of PAA and glycerin to ionomeric particulates. The adhesive coating weight was about 116 grams/m$^2$. The cosmetic strips were efficacious in removing comedomes from the pores of the users' skin.

Examples 6a to 6f

Examples 6a to 6f examined the various molecular weights of polyacrylic acid and blends of polyacrylic acid (PAA). The molecular weight reported in Table 2 came from the manufacturer's literature. The ionomer particulate composition was made according to Example 1b.

To a vessel equipped with a mixing device, about 50 grams of the ionomeric particulate was charged. The PAA solution, the amounts described in Table 2 were added. About 0.8 grams of polyethylene glycol (PEG) (Carbowax 600, from Union Carbide Co.) was added as the plasticizer.

The dispersion and the cosmetic strips were made according to the methods described in Example 2 except that the backing material was a spunlaced non-woven rayon-polyester blend (SONTARA® 8423 from E. I. du Pont, Wilmington, Del.). Table 2 lists the various PAA, the amounts of PAA, and the amounts of isopropanol co-solvent used, all weights being in grams. The resulting cosmetic adhesive components contained about 90:10 solids weight ratio of PAA to plasticizer and about a 27:73 solids weight ratio of PAA and PEG to ionomeric particulates. All the cosmetic strips were efficacious in removing comedomes from the pores of the users' skin.

added. About 0.3 grams of polyethylene glycol (Carbowax 600, from Union Carbide Co., Danbury, Conn.) was added to the vessel. The resulting dispersion was coated and the cosmetic strips were made according to the method described in Example 2. The adhesive coating weight was about 105 grams/m$^2$. The cosmetic strips were efficacious in removing comedomes from the pores of the users' skin.

Example 8

A 6% solids by weight solution of magnesium citrate was prepared by adding SS-3130 Magnesium Citrate Tribasic, USP (from Jost Chemical, St. Louis, Mo.) to an appropriate amount of deionized water. To about 50 grams of dispersion of Example 7 was added about 1.7 grams of the previously prepared magnesium citrate solution. The resulting dispersion was coated and the cosmetic strips were made according to the method described in Example 2. The adhesive coating weight was about 96 grams/m$^2$. The cosmetic strips were efficacious in removing comedomes from the pores of the users' skin.

Example 9

To a vessel equipped with a mixing device, about 50 grams of ionomeric particulate made according to Example 1a was charged. About 13.2 grams of a 19% solids by weight solution of PAA having a molecular weight of about 500,000 was added while stirring was continued. The PAA was made according to Example 3 of U.S. Pat. No. 2,838,421 (Sohl). About 0.3 grams of polyethylene glycol, PEG, (Carbowax 600, from Union Carbide Co., Danbury, Conn.) plasticizer was added to the vessel. About 9.5 grams of isopropanol was added as a co-solvent. The resulting dispersion and the

TABLE 2

Various Types of PAA for Cosmetic Adhesive

| EX | Coating Weight (g/m$^2$) | Co-Solvent (grams) | Amount | Tradename | Description | Molecular Weight |
|---|---|---|---|---|---|---|
| 6a | 117 | 13.3 | 38.58 | Sokalan ® CP 13 S$^a$ (25% solids by wt) | modified PAA | 20,000 |
| 6b | 121 | 11.6 | 27.55 | Sokalan PA 80 S$^a$ (35% solids by wt) | PAA | 100,000 |
| 6c | 125 | 11.6 | 27.55 | Sokalan PA 110 S$^a$ (35% solids by wt) | PAA | 250,000 |
| 6d | 117 | 17.1 | 42.49 | Carbopol ® 907$^b$ (15% solids by wt as prepared in Ex. 2) | PAA | 450,000 |
| 6e | 81 | 15.1 | 50.76 | Example 3 of U.S. Pat. No. 2,838,421 (19% solids by wt) | PAA | 500,000 |
| 6f | 111 | 12.2 | 31.24 | Sokalan PA 80 S$^a$/ Carbopol 907 (as described above) | PAA 90/10 blend | Blend of 100,000 and 450,000 |

$^a$from BASF Co., Mt. Olive, NJ
$^b$from B. F. Goodrich, Cleveland, OH

Example 7

A 25/75 blend of PAA solution was prepared by mixing the 15% solids by weight solution of Carbopol® 907 (made as described in Example 2) to the Good-Rite® K-702. To a vessel equipped with a stirring, about 50 grams of ionomeric particulate made according to Example 1c was charged. About 3 grams of an opacifying additive (ROPAQUE® OP-96, from Rohm and Haas) was added to the vessel. About 46.6 grams of the previously prepared PAA blend was cosmetic strips were made according to the method described in Example 2. The resulting cosmetic adhesive contained about 90:10 solids weight ratio of PAA to plasticizer and about 11:89 solids weight ratio of PAA and PEG to ionomeric particulate ratio. The adhesive coating weight was about 125 grams/m$^2$. The cosmetic strips had lower apparent adhesion to skin than the strips prepared from Example 6e and were efficacious in removing comedomes from the pores of the users' skin.

Example 10

The ionomeric particulate was prepared according to Example 1a except that about 0.625 grams of polyacrylamide dispersion (Cyanomer® N-300, from Cytec Industries, West Paterson, N.J.) was added to the water phase.

To a vessel equipped with a mixing device, about 50 grams of ionomeric particulate was charged. About 49.93 grams of PAA having a molecular weight of about 450,000 (Carbopol® 907 from B. F. Goodrich, Cleveland, Ohio, at about 15% solids by weight as prepared according to Example 2) was added while stirring was continued. About 0.83 grams of polyethylene glycol, PEG, (Carbowax 600, from Union Carbide Co., Danbury, Conn.) plasticizer was added to the vessel. About 15.1 grams of isopropanol was added as a co-solvent. The resulting dispersion and the pore-cleaning strips were made according to the method described in Example 2. The resulting adhesive contained about 90:10 solids weight ratio of PAA to plasticizer and about 27:73 solids weight ratio of PAA and PEG to ionomeric particulate. The adhesive coating weight was about 124 grams/m$^2$. The pore-cleaning strips were efficacious in removing comedomes from the pores of the users' skin.

Example 11

A 15% solids by weight solution of a hydrolyzed methylvinylether and maleic anhydride copolymer (PVM/MA) (Gantrez® S-97 from International Specialty Products, Wayne, N.J.) was prepared in de-ionized water. This copolymer served as the polymer matrix, i.e., the continuous phase.

To a vessel equipped with a mixing device, about 50 grams of ionomeric particulate made according to Example 1b was charged. About 44.4 grams of hydrolyzed PVM/MA solution was added while stirring was continued. About 0.74 grams of polyethylene glycol, PEG, (Carbowax 600, from Union Carbide Co., Danbury, Conn.) plasticizer was added to the vessel. About 14.3 grams of isopropanol was added as a co-solvent. The resulting dispersion and the cosmetic strips were made according to the method described in Example 2 except that the backing material was a spunlaced non-woven rayon polyester blend (SONTARA® 8423 from E. I. du Pont de Nemours and Co., Wilmington, Del.). The resulting adhesive contained about 90:10 solids weight ratio of the acid containing copolymer to plasticizer and about 23:73 solids weight ratio of PVM/MA and PEG to ionomeric particulate. The adhesive coating weight was about 98 grams/m$^2$. The cosmetic strips were efficacious in removing comedomes from the pores of the users' skin.

Example 12

A 25/75 blend of PAA solution blend was prepared by mixing the 15% solids by weight solution of Carbopol® 907 (made as described in Example 2) to the Good-Rite® K-702. To a vessel equipped with a stirring, about 50 grams of ionomeric particulate made according to Example 1d was charged. About 3 grams of an opacifying additive (ROPAQUE® OP-96, from Rohm and Haas) was added to the vessel. About 33.1 grams of the previously prepared PAA blend was added. About 0.3 grams of polyethylene glycol (Carbowax 600, from Union Carbide Co., Danbury, Conn.) was added to the vessel. The resulting dispersion was coated and the cosmetic strips were made according to the method described in Example 2. The adhesive coating weight was about 114 grams/m$^2$. The cosmetic strips were efficacious in removing comedomes from the pores of the users' skin.

Examples 13a to 13d

These examples show the use of a hydrophobic layer in a cosmetic strip.

In Example 13a, a hydrophobic material, SCOTCHGUARD® product number 3572ES, was sprayed evenly onto a second surface of a spunlaced non-woven polyester backing (SONTARA® 8017 from Du Pont). The sample was placed in a forced air oven at about 150° F. (65° C.) until dry, about 5 to 10 minutes. An adhesive made according to Example 2 was laminated to the second side of the treated backing.

In Example 13b, the SCOTCHGUARD® 3572ES was sprayed on the first surface (i.e., the exposed surface) of an adhesive made according to Example 2. The treated adhesive was immediately laminated to the SONTARA® 8017 backing, the lamination step as described in Example 2.

In Example 13c, a hydrophobic material, GE product number SM 2059 (believed to be silicone water-based emulsions at about 35% solids) was applied to the first surface of an adhesive made according to Example 2. The application involved immersing a cotton cloth with the hydrophobic material and wiping it onto the adhesive. The treated side of the adhesive was laminated to a SONTARA® 8017 backing as described in Example 2.

In Example 13d, the hydrophobic material was made according to U.S. Pat. No. 2,532,011 (Dahlquist et al.), which disclosed low adhesion polyvinyl carbamate coatings. A cosmetic strip was prepared as in Example 2. To the first side (i.e., exposed side) of the SONTARA® 8017 backing, a small quantity (about 3–5 drops from a dropper) of the hydrophobic material was applied. The sample was placed in the nip of a hand-held precision hand proofer (from Pamarco Inc., Roselle, N.J.) to force the hydrophobic material into the backing. The treated sample was placed in a forced air oven at about 150° F. (65° C.) until dry, about 5 to 10 minutes.

To the exposed surface of the backings of Examples 13a to 13d, water droplets were applied. The droplets remained on the surface of the backings for about 3 to 5 minutes before starting to soak into the backing.

Test Methods

The following test methods were used to characterize the repulpable tape.

Shear Strength

Shear strength is a measure of the cohesiveness or internal strength of an adhesive. It is based upon the amount of force required to pull an adhesive strip from a standard flat surface in a direction parallel to the surface to which it has been affixed with a definite pressure. It is measured in terms of time (e.g., in minutes) required to pull a standard area of adhesive coated sample from a cleaned stainless steel test panel where the sample is subjected to a constant, standard force.

The shear strength test is similar to that of ASTM D 3654-88. Adhesive coatings on polyester film were cut into 1.27 cm (0.5 in.) by 15 cm (6 in.) strips. Each strip was then adhered to a stainless steel panel such that a 1.27 cm by 1.27 cm portion of each strip was in firm contact with the panel and one end portion of the tape being free. The panel with coated strip attached was held in a rack such that the panel formed an angle of 178° with the extended tape free end which was tensioned by application of a force of one kilogram applied as a hanging weight from the free end of the coated strip. The 2° less than 180° was used to negate any peel forces, thus ensuring that only shear strength forces were measured, in an attempt to determine more accurately the holding power of the adhesive being tested. The time elapsed for each tape example to separate from the test panel was recorded as the shear strength. All shear strength failures (if the adhesive failed at less than 10,000 minutes) reported herein were cohesive failures of the adhesive. Each test was terminated at 10,000 minutes, unless the adhesive failed at an earlier time (as noted).

TAPPI Repulpability Test Method UM-213

For a double-faced tape, one 20 cm by 2.54 cm strip of adhesive is sandwiched between two 20 cm by 2.54 cm strips of blotter paper. For a single-faced tape, two 20 cm by 2.54 cm adhesive strips are adhered to blotter paper. The samples are cut into approximately 1.5 cm squares. A sufficient number of 1.5 cm squares were added to the adhesive/blotter paper combination to provide a total test sample weight of about 15 grams. The test sample is then placed in a Waring™ blender with about 500 milliliters of room temperature tap water. After the blender ran for about 20 seconds, it is stopped for about 1 minute while the stock that has splashed up the sides and on the cover of the blender is washed back into the bottom with some water. The blender ran for an additional 20 seconds, washed down as before, and ran for a final 20 seconds. The stock is removed from the blender and made into a hand-sheet on a sheet mold. The sheet is removed from the mold, pressed between blotter paper for 90 seconds in a hydraulic press, dried, and examined for any unrepulped tape. If two or fewer particles are present, the tape passed the test. The presence of one or two particles does not constitute failure because these particles can be due to dirty equipment or screens.

This repulpability test does not apply to tape products where the backing is a material, such as polyester film, which does not lend itself to repulping. The dispersibility of the adhesive used on such a backing may be determined by testing the adhesive either in the form of an adhesive transfer tape or as a layer on a water-dispersible support layer.

Japanese Repulpability Test

About 2.0 grams of the sample repulpable adhesive (including backing but without liner) was adhered to a #2 filter paper. If the sample adhesive was a double-coated tape, another #2 filter paper was adhered so that the adhesive was sandwiched between two #2 filter papers. The filter paper with the 2.0 grams of adhesive was cut into 20 mm square pieces with a razor or other suitable cutting means. A sufficient number of 20 mm squares were added to the adhesive/filter paper combination to provide a total test sample weight of about 26.0 grams.

An aqueous dispersion of the repulpable adhesive was made as follows. First a pH 7.0 solution was made by mixing about 1.8 liters of water with about 0.7 grams of aluminum sulfate and about 0.2 liters of a buffer solution standard (pH 4.0) for about 3 minutes. To a pulper kettle (British Evaluation Apparatus, from Manis Engineering, LTD, London, UK) was added the previously cut 26.0 grams of sample and about 2.0 liters of the pH 7.0 solution. The pulper kettle was again placed in the British Evaluation Apparatus and run at about 3000 rpm for about 150 seconds to produce an aqueous dispersion.

To perform the paper-sheeting test, a steel mesh filter was first set in the bottom of the JIS paper-sheeting machine (Sheet Mold, from Williams Apparatus Co., Watertown, N.Y.). About 2.0 liters of water was combined with about 0.5 liter of the aqueous dispersion and poured into the paper-sheeting machined. Mix the water and the aqueous dispersion by hand using a metal rake. Wait about 2 minutes for the most of the air bubbles to dissipate. Pour about 100 milliliter of the dispersion through the steel mesh filter. The paper has now been re-sheeted on the steel mesh filter. Sandwich the re-sheeted paper between two #26 filter papers. Apply a pressure of about 5 kg/cm² to the sandwiched re-sheeted paper for about 5 minutes. The re-sheeted paper was dried with a heated drum dryer at about 100° C. (212° F.) for about 5 to 10 minutes. Examine the dried, re-sheeted paper and classify it as follows: (1) "excellent" if there is no tack, no color, and no pin-hole, (2) "fair" is there is some remaining tack but only at the edge of the re-sheeted paper, or there is pin-hole of 1 to 2 mm², and (3) "fail" if there is remaining tack at the surface of the re-sheeted paper.

Examples 14 to 19

Examples 14 to 19 show different formulations of repulpable adhesive. The ionomeric particulates were made by a suspension polymerization reaction. The reaction was carried out in a 2-liter split-flask equipped with a condenser, thermometer, nitrogen inlet, motor-driven agitator, and a heating mantle with temperature control. The reaction flask was first charged with the ingredients of the aqueous phase, as shown in Table 3, and heated to 58° C. The batch of aqueous phase was maintained at this temperature with agitation and nitrogen-purging for about 1 hour to remove oxygen from the flask. Afterwards, a premixed charge of the oil phase, as shown in Table 3, was added to the flask while vigorous agitation (700 rpm) was maintained to obtain a good suspension. The ensuing suspension polymerization reaction was continued with nitrogen purging. After exotherm, the reaction was continued at 75° C. for about another 2 hours, and then the reaction mixture was cooled to room temperature. The ionomeric particulate composition was stored in aqueous form. The suspension polymerization produced an aqueous suspension of ionomeric particulate having about 40% solids by weight.

To a vessel equipped with a mixing device, about 68.49 parts of the ionomeric particulate was charged. About 21.66 parts of polyacrylic acid (made according to Example 3 of U.S. Pat. No. 2,838,421 (Sohl)), which is hereby incorporated by reference in its entirety. About 9.95 parts of polyethylene glycol (Carbowax™ 550, from Union Carbide Co., Danbury, Conn.) was added. The resulting dispersion was notch coated to a paper liner (50# D2B paper liner from Akrosil Co.) at a gap setting of about 0.3 mm. The coated web was dried for about 5 minutes at a temperature of about 80° C. to yield a repulpable tape. The tape was tested for shear strength and repulpability (TAPPI test method UM-213).

TABLE 3

Ionomeric Particulates for Repulpable Adhesive

| Ingredients, grams: | EXAMPLES | | | | | |
|---|---|---|---|---|---|---|
| | 14 | 15 | 16 | 17 | 18 | 19 |
| Water phase: | | | | | | |
| Water (deionized) | 600 | 600 | 600 | 600 | 600 | 600 |
| Methacrylic acid | 20 | 20 | 20 | 20 | 20 | 20 |
| Zinc oxide | 2 | 1 | 0 | 2 | 2 | 2 |
| Colloidal silica[a] | 2 | 2 | 2 | 2 | 2 | 2 |
| Sodium styrene sulfonate | 20 | 20 | 20 | 20 | 20 | 20 |
| Sodium dodecylbenzene sulfonate[b] | 4.3 | 4.4 | 4.4 | 4.4 | 4.4 | 4.4 |
| Isooctyl thioglycolate | 0 | 0 | 0 | 0.33 | 0.16 | 0.04 |
| Oil Phase: | | | | | | |
| Isooctyl acrylate | 380 | 380 | 380 | 380 | 380 | 380 |
| 2,2'-Azobis(2- | 1.6 | 1.6 | 1.6 | 1.6 | 1.6 | 1.6 |

TABLE 3-continued

Ionomeric Particulates for Repulpable Adhesive

| | EXAMPLES | | | | | |
|---|---|---|---|---|---|---|
| Ingredients, grams: | 14 | 15 | 16 | 17 | 18 | 19 |
| methylbutyronitrile)[c] | | | | | | |
| Volume average particle size, $\mu$m | 8 | 6 | 7 | 7 | 8 | 9 |
| Shear (minutes to failure) | >2800 | 1100 | 350 | >2800 | 1850 | 2450 |
| Repulpability (Yes-No) | yes | NA[d] | NA[d] | no | no | yes |

[a]Nalco ™ 1042 colloidal silica, from Nalco Chemical Company, Naperville, IL
[b]Rodacal DS-10 from Rhone-Poulenc, Cranbury, NJ
[c]Vazo ™ 67 initiator, from du Pont de Nemours and Company, Wilmington, DE
[d]Not tested Examples 14, 15, and 16 contained ZnO in an amount of about 0.5, 0.25, and 0 parts, based on the total adhesive composition, respectively. The repulpability of Examples 15 and 16 were not tested for repulpability performance at this time. Examples 17, 18, and 19 all used varying amounts of an added chain transfer agent, isooctyl thioglycolate (IOTG), at about 0.08, 0.04, and 0.01 parts, based on the total adhesive composition, respectively. It was only at the very low levels of IOTG (0.01 parts) that the adhesive passed the TAPPI test.

Example 20

The ionomeric particulates were made according to Example 14 above. To a vessel equipped with a mixing device, about 72 parts of the ionomeric particulate was charged. About 21.3 parts of polyacrylic acid (MC-810 from 3M, St. Paul, Minn.) was added. About 6.7 parts of polyethylene glycol (Carbowax™ 550, from Union Carbide Co., Danbury, Conn.) was added. The resulting dispersion was notch coated to a first side of a paper liner (50# D2B paper from Akrosil Co.) at a gap setting of about 0.2 mm. The coated web was dried for about 5 minutes at a temperature of about 80° C. A light-weight paper scrim (#9 tissue paper) was then laminated to the adhesive surface and the dispersion was again notch bar coated at the same gap setting onto the paper scrim. The entire construction was dried at the same conditions to yield a double-sided repulpable tape.

Example 21

The ionomeric particulates were made according to Example 14 above. To a vessel equipped with a mixing device, about 68.5 parts of the ionomeric particulate was charged. About 21.7 parts of polyacrylic acid (MC-810 from 3M, St. Paul, Minn.) was added. About 9.95 grams of polyethylene glycol (Carbowax™ 550, from Union Carbide Co., Danbury, Conn.) was added. The resulting dispersion was notch coated to a paper liner (50# D2B from Akrosil Co.) at a gap setting of about 0.3 mm to make a single coated tape. The coated web was dried for about 5 minutes at temperature of about 80° C. For a double-coated tape, the dispersion of this example was coated according to the method described in Example 16.

The tape was tested according to the Japanese test method JTM-0255-B and passed the test.

All references cited above, including patents discussed in the Background, are incorporated by reference in their entirety into this document.

The present invention may be suitably practiced in the absence of any element or item not specifically described in this document.

What is claimed is:

1. An organic particulate-filled adhesive comprising ionomeric particulates dispersed in a polymer matrix further comprising water-soluble polymer, the ionomeric particulate comprising the reaction product of:
    (a) at least one vinyl monomer selected from the group consisting of acrylic acid ester of non-tertiary alcohol having 1 to 14 carbon atoms, vinyl acetate, styrene, octylacrylamide, and N-vinyl lactams;
    (b) at least one acid monomer containing a carboxylic acid;
    (c) at least one metal oxide;
    (d) at least a first and a second surfactant, the first surfactant being a monomer surfactant that aids in the initial formation of the ionomeric particulate and at least a portion of the first surfactant polymerizes to become a part of the ionomeric particulate; and
    (e) at least one initiator.

2. The adhesive of claim 1 comprising from about 60 to 95 parts by weight ionomeric particulate and from about 5 to 40 parts by weight polymer matrix.

3. The adhesive of claim 1, wherein the metal oxide is present in an amount sufficient to fully neutralize the acid monomer.

4. The adhesive of claim 1, wherein the reaction product further comprises polyacrylamide.

5. The adhesive of claim 1, wherein the ionomeric particulate has an average particle size of about 1 to 10 micrometers.

6. The adhesive of claim 1, wherein the reaction product further comprises metal salts of carboxylic acid containing a metal cation.

7. The adhesive of claim 6, wherein the metal cation is selected from the group consisting of magnesium, calcium, and zinc.

8. The adhesive of claim 6, wherein the metal salts of carboxylic acid is present in an amount of about 0.01 to 5 parts by weight.

9. The adhesive of claim 1 further comprising a plasticizer.

10. The adhesive of claim 9 comprising from about 65 to at most 90 parts by weight of the ionomeric particulate, from about 5 to at most 40 parts by weight of the water-soluble polymer, and at most about 40 parts by weight of the plasticizer, the amount of plasticizer being based on the amount of water-soluble polymer.

11. The adhesive of claim 10, wherein the plasticizer is selected from the group consisting of polyethylene glycol, glycerin, polypropylene glycol, polypropylene glycol-polyethylene oxide copolymer, block copolymers of ethylene oxide and propylene oxide, polyethylene oxide alkylphenyl ethers, water, and combinations thereof.

12. The adhesive of claim 10, wherein the water-soluble polymer is selected from the group consisting of polyacrylic acid, salts of polyacrylic acid, polymethacrylic acid, sulfonated polyester, polysodium 2-acrylamido-2-methylpropane sulfonate, polyethylene oxide, polyvinyl pyrrolidone, gamma radiation modified polyvinyl pyrrolidone, polyvinyl methyl ether-maleic anhydride copolymer, polyvinyl alcohol, polydimethylamino methacrylate, and combinations thereof.

13. The adhesive of claim 12, wherein the water-soluble polymer has a molecular weight from about 100,000 to 500,000.

14. The adhesive of claim 10, further comprising at least one additive selected from the group consisting of opacifying agent, skin conditioning agent, skin cleansing agent, vitamins, herbal extracts, anti-inflamatories, and combinations thereof.

15. The adhesive of claim 14 wherein the additive is present in an amount of about 0.001 to 10 parts by weight.

16. The adhesive of claim 14, wherein the opacifying agent is styrene-acrylic copolymer hollow particles.

17. The adhesive of claim 16, wherein the opacifying agent is present in an amount of about 0.6 to 6.0 parts per hundred, based on the total adhesive weight.

18. A cosmetic strip comprising:
   (a) a flexible backing having a first surface and a second surface; and
   (b) the adhesive of claim 10 disposed on at least a portion of the first surface of the flexible backing.

19. The cosmetic strip of claim 18 further comprising a hydrophobic layer disposed on at least a portion of the second surface of the flexible backing.

20. The cosmetic strip of claim 19 wherein the hydrophobic layer is selected from the group consisting fluoropolymer, fluorosilicone, silicone, paraffin, polyethylene, polypropylene, ethylene-acrylic copolymers, polyurethane, urethane-acrylate copolymers, acrylate copolymers, methacrylate copolymers, and combinations thereof.

21. The cosmetic strip of claim 18, wherein the flexible backing is selected from the group consisting of spunlaced non-woven, spun-bonded non-woven, polyurethane open-celled foams, carded web non-woven, blown microfiber non-woven, woven fabrics selected from the group consisting of cotton, acetate, polyester, and combinations thereof.

22. The adhesive of claim 9 comprising from about 65 to at most 90 parts by weight of ionomeric particulate, from about 5 to at most 40 parts by weight of water-soluble polymer, and at least about 40 parts by weight of the plasticizer, the amount of plasticizer based on the amount of water-soluble polymer, and wherein the adhesive is repulpable when tested according the Japanese Repulpability Test Method.

23. The adhesive of claim 22, wherein the water-soluble polymer matrix is selected from the group consisting of polyacrylic acid, salts of polyacrylic acid, polymethacrylic acid, sulfonated polyester, polysodium 2-acrylamido-2-methylpropane sulfonate, polyethylene oxide, polyvinyl alcohol, polydimethylamino methacrylate, and combinations thereof.

24. The adhesive of claim 23, wherein the water-soluble polymer has a molecular weight in the range of about 200,000 to 500,000.

25. An organic particulate-filled adhesive comprising ionomeric particulates dispersed in a polymer matrix further comprising water-dispersible polymer, the ionomeric particulate comprising the reaction product of:
   (a) at least one vinyl monomer selected from the group consisting of acrylic acid ester of non-tertiary alcohol having 1 to 14 carbon atoms, vinyl acetate, styrene, octylacrylamide, and N-vinyl lactams;
   (b) at least one acid monomer containing a carboxylic acid;
   (c) at least one metal oxide;
   (d) at least a first and a second surfactant, the first surfactant being a monomer surfactant that aids in the initial formation of the ionomeric particulate and at least a portion of the first surfactant polymerizes to become a part of the ionomeric particulate; and
   (e) at least one initiator.

* * * * *